(12) United States Patent
Kawasaki et al.

(10) Patent No.: US 7,741,246 B2
(45) Date of Patent: Jun. 22, 2010

(54) HERBICIDE COMPOSITION AND WEED-CONTROLLING METHOD USING THE SAME

(75) Inventors: Hiroshi Kawasaki, Tokyo (JP); Takeshige Miyazawa, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 668 days.

(21) Appl. No.: 10/507,929

(22) PCT Filed: Mar. 24, 2003

(86) PCT No.: PCT/JP03/03541
§ 371 (c)(1), (2), (4) Date: Sep. 17, 2004

(87) PCT Pub. No.: WO03/079784
PCT Pub. Date: Oct. 2, 2003

(65) Prior Publication Data
US 2005/0170964 A1    Aug. 4, 2005

(30) Foreign Application Priority Data
Mar. 27, 2002   (JP)   ............................ 2002-088886

(51) Int. Cl.
*A01N 43/00* (2006.01)
*A01N 43/72* (2006.01)
*A01N 37/18* (2006.01)

(52) U.S. Cl. ..................... 504/139; 504/116.1; 504/118; 504/129; 504/130; 504/149; 504/132; 504/138

(58) Field of Classification Search ................. 504/128, 504/136, 134, 118, 129, 139, 130, 132, 138, 504/149
See application file for complete search history.

(56) References Cited

U.S. PATENT DOCUMENTS 5,362,704 A * 11/1994 Goto et al. .................. 504/134
2005/0090396 A1 * 4/2005 Feucht et al. ............... 504/129

FOREIGN PATENT DOCUMENTS

| EP | 1101760 A1 * | 5/2001 |
| JP | 2000-281513 | 10/2000 |
| JP | 2001-233718 | 8/2001 |
| WO | WO 0003592 A * | 1/2000 |
| WO | 00/40085 | 7/2000 |

* cited by examiner

*Primary Examiner*—Johann R Richter
*Assistant Examiner*—Danielle Sullivan
(74) *Attorney, Agent, or Firm*—Wenderoth, Lind & Ponack, L.L.P.

(57) ABSTRACT

Provided is a herbicide composition which comprises a combination in a specific proportion of 2-[(4,6-dimethoxypyrimidin-2-yl)hydroxymethyl]-6-methoxymethyl-N-difluoromethanesulfonylanilide as the component (A) and either one of fifteen kinds of compounds including 4-(2-chlorophenyl)-N-cyclohexyl-N-ethyl-4,5-dihydro-5-oxo-1H-tetrazole-1-carboxamide as the component (B), none of which has been used in combination with the compound as the component (A). By an application of the herbicide composition to a paddy field in a specific dose, an excellent herbicidal effect is obtained against various kinds of weeds growing in paddy fields and the chemical damages thereof to paddy rice is extremely low.

4 Claims, No Drawings

HERBICIDE COMPOSITION AND WEED-CONTROLLING METHOD USING THE SAME

TECHNICAL FIELD

The invention relates to an novel herbicide composition and a method for weed-controlling by using the same, more particularly, to a novel herbicide composition capable of effectively preventing weed growth and removing various types of weeds growing in paddy fields even only by one time dispensation without inhibiting growth of rice and to a method for weed-controlling weeds in paddy fields by dispensing the herbicide composition in paddy fields.

BACKGROUND ART

Various kinds of herbicides have been developed so far and have contributed to agricultural productivity and laborsaving. However, since there are some kinds of herbicides which have been used so many years, some weeds have become resistant to them and hardly destroyable weeds against which those herbicides are not or little effective have been increasing and therefore, it has been highly expected to develop herbicides having a wide herbicide spectrum and effective even against these hardly destroyable weeds.

Further, conventional herbicides often cause pollution of soil and ambient environmental pollution and, in order to prevent such environmental pollution, development of herbicides highly active and effective even in a small amount of use has been desired.

Besides, to deal with uneven propagation of weeds over a long time, herbicides having excellent effect retention, effective even by dispensation in a wide range of periods from before development of weeds to the growing stage and having a wide range of appropriate application period have been expected to be available.

Moreover, it is well known that with respect to use of conventional herbicides, chemical damages are sometimes caused on crops depending on a variety of factors relative to weather conditions such as temperature, wind, light and the like; soil conditions such as soil properties, organic compound contents in soil and the like; planting management conditions such as shallow transplantation depth, use of fragile and too long seedling, deep water control and the like; conditions for application of the chemical agent such as uneven sprinkling or excess sprinkling of herbicides and the like, so that appearance of a herbicide highly safe and free from a risk of occurrence of chemical damages on crops in any conditions has been desired.

DISCLOSURE OF THE INVENTION

The present invention has an object to provide a herbicide composition, especially, a herbicide composition for removing weeds growing in paddy fields and a weed-controlling method using the same for removing weeds in paddy fields.

As a result of earnest investigations made to satisfy the above-mentioned expectations, the inventors of the invention have found that when 2-[(4,6-dimethoxypyrimidin-2-yl)hydroxymethyl]-6-methoxymethyl-N-difluoromethanesulfonylanilide, which is known as an effective ingredient for a herbicide, is used singly, no effective weed-controlling on weeds grown to an advanced state or perennial weeds growing in paddy fields is obtained unless it is used in a high concentration and therefore, chemical damages are caused on rice, while unexpectedly, only a single dispensation thereof in a low concentration in combination with certain kinds of compounds can prevent growth of a wide spectrum of weeds growing in paddy fields or remove them over a long time and that rice is not damaged and based on the findings, the inventors have accomplished the invention.

That is, the invention provides a herbicide composition characterized by containing, as effective ingredients, (A) 2-[(4,6-dimethoxy-pyrimidin-2-yl)hydroxymethyl]-6-methoxymethyl-N-difluoromethanesulfonylanilide; and (B) at least one kind of compound selected from:

(1) 4-(2-chlorophenyl)-N-cyclohexyl-N-ethyl-4,5-dihydro-5-oxo-1H-tetrazole-1-carboxamide (common name: fentrazamide), (2) 3-[1-(3,5-dichlorophenyl)-1-methylethyl]-3,4-dihydro-6-methyl-5-phenyl-2H-1,3-oxazin-4-one (common name: oxaziclomefone), (3) O-3-tert-butylphenyl 6-methoxy-2-pyridyl(methyl)-thiocarbamate (common name: pyributicarb), (4) O-ethyl O-6-nitro-m-tolyl(RS)-sec-butylphosphoramidothioate (common name: butamifos), (5) S-4-chloro-N-isopropylcarbaniloylmethyl O,O-dimethyl phosphorodithioate (common name: anilofos), (6) methyl 5-(2,4-dichlorophenoxy)-2-nitrobenzoate (common name: bifenox), (7) 5-tert-butyl-3-[2,4-dichloro-5-(prop-2-ynyloxy)phenyl]-1,3,4-oxadiazol-2(3H)-one (common name: oxadiargyl), (8) 3-(2-chloro-4-mesylbenzoyl)-2-phenylthiobicyclo[3.2.1]oct-2-en-4-one (common name: benzobicyclon), (9) S,S'-dimethyl 2-difluoromethyl-4-isobutyl-6-trifluoromethylpyridine-3,5-dicarbothioate (common name: dithiopyr),

(10) S-ethyl azepane-1-carbothioate (common name: molinate),

(11) 2-amino-3-chloro-1,4-naphthoquinone (quinoclamine),

(12) methyl 2-[(4,6-dimethoxypyrimidin-2-yl)oxy]-6-[1-(methoxyimino)ethyl]benzoate (common name: pyriminobac-methyl),

(13) methyl α-(4,6-dimethoxypyrimidin-2-ylcarbamoylsulfamoyl)-o-toluate (common name: bensulfuron-methyl),

(14) ethyl 5-(4,6-dimethoxypyrimidin-2-ylcarbamoylsulfamoyl)-1-methylpyrazole-4-carboxylate (common name: pyrazosulfuron-ethyl), and

(15) (RS)-7-(4,6-dimethoxypyrimidin-2-ylthio)-3-methyl-2-benzofuran-1(3H)-one (common name: pyriftalid)

and a weed-controlling method characterized by removing weeds in a paddy field by sprinkling this herbicide composition to a paddy field.

BEST MODE FOR PRACTICING OF THE INVENTION

A sulfonylanilide derivative to be used as the component (A) in the invention is a compound capable of exhibiting an excellent weed-controlling effect in a low concentration and having a wide herbicidal spectrum (Japanese Patent Application Laid-Open No. 2000-44546) but, however, it is needed to dispense it in a high concentration to prevent growth of weeds having grown to an advanced state and perennial weeds and remove them and in the case of its use in a high concentration, there occurs a problem that the safety to rice is degraded.

However, when it is used in combination with either one of the compounds (1) to (15) as the component (B) aforementioned, even if it be used in a low concentration, an excellent weed-controlling effect even on weeds grown to an advanced state and perennial weeds can be achieved and dispensation can be carried out safely for rice.

Use of the herbicide composition of the invention exhibits a weed-controlling effect quickly as compared with that in the case where each of the single agents is used and weed controlling can be quickly performed. Moreover, the herbicide composition shows a weed-controlling effect so high as not to be obtained with one of the respective agents containing a single kind of the compounds and a wide herbicidal spectrum is obtained.

When the herbicide composition of the invention is used as a herbicide for rice crops, the range of appropriate application period of the chemical agent is so wide as compared with existing herbicides for rice crops as to exhibit a high herbicidal activity against hardly destroyable weeds from before germing to the growing stage inhibiting generation of the weeds over a long time still without inhibition of the growth of crop plants.

That is, the herbicide composition of the invention can prevent growth of and remove annual weeds in paddy fields such as weeds of the family of Gramineae including *Echinochloa* species such as early watergrass (*Echinochloa oryzicola*), barnyardgrass (*Echinochloa crus-galli* var. *crus-galli*) and the like; *Cyperus* species such as smallflower umbrella plant (*Cyperus difformis*), HINA-GAYATSURI (*Cyperus flaccidus*) and the like; weeds of the family of Pontederiaceae such as heartshape false pickerelweed (*Monochoria vaginalis*), MIZU-AOI (*Monochoria korsakowii*) and the like; weeds of the family of Scrophulariaceae such as *Linderina* species, dopatrium (*Dopatrium junceum*) and the like; weeds of the family of Lythraceae such as indian toothcup (*Rotala indica*), HIME-MISO-HAGI (*Ammannia multiflora*) and the like; MIZO-HAKOBE (*Elatine triandra*) and others; as well as perennial weeds such as weeds of the family of Alismataceae such as URIKAWA (*Sagittaria pygmaea*), arrow head (*Sagittaria trifolia*) and the like; weeds of the family of Cyperaceae such as MIZU-GAYATSURI (*Cyperus serotinus*), SHIZUI (*Scirpus nipponicus*), KUROGUWAI (*Eleocharis kuroguwai*), INU-HOTARU-I (*Scirpus juncoides*), KOUKIYAGARA (*Scirpus planiculmis*), needle spikerush (*Eleocharis acicularis*) and the like; roundleaf pondweed (*Potamogeton distinctus*); SERI (*Oenanthe javanica*) and others over a long period of time from before germing to the growing stage and exhibits high safety to rice.

The mixing ratio of the components (A) and (B) in the herbicide composition of the invention is different depending on the types and states of weeds, the dispensation period and method, formulation forms and the like and it is necessary to select a mixing ratio and a dispensation amount in the wide range according to need.

As a mixing ratio, it is, usually, selected in the range of 0.1 to 500 parts by mass, preferably, 0.2 to 200 parts by mass or, more preferably, 0.5 to 100 parts by mass of the component (B) per 1 part by mass of the component (A).

To describe in more details, it is preferable to use, per 1 part by mass of the component (A), in the case of the compound (1), 0.5 to 20 parts by mass or, preferably, 1 to 15 parts by mass; in the case of the compound (2), 0.5 to 20 parts by mass or, preferably, 0.5 to 5 parts by mass; in the case of the compound (3), 5 to 100 parts by mass or, preferably, 5 to 30 parts by mass; in the case of the compound (4), 5 to 100 parts by mass or, preferably, 10 to 50 parts by mass; in the case of the compound (5), 5 to 100 parts by mass or, preferably, 5 to 30 parts by mass; in the case of the compound (6), 5 to 100 parts by mass or, preferably, 10 to 50 parts by mass; in the case of the compound (7), 0.5 to 20 parts by mass or, preferably, 0.5 to 5 parts by mass; in the case of the compound (8), 0.5 to 20 parts by mass or, preferably, 1 to 15 parts by mass; in the case of the compound (9), 0.5 to 20 parts by mass or, preferably, 0.5 to 5 parts by mass; in the case of the compound (10), 5 to 100 parts by mass or, preferably, 15 to 60 parts by mass; in the case of the compound (11), 5 to 100 parts by mass or, preferably, 10 to 70 parts by mass; in the case of the compound (12), 0.5 to 20 parts by mass or, preferably, 0.5 to 10 parts by mass; in the case of the compound (13), 0.5 to 20 parts by mass or, preferably, 0.5 to 5 parts by mass; in the case of the compound (14), 0.5 to 20 parts by mass or, preferably, 0.5 to 5 parts by mass; and in the case of the compound (15), 0.5 to 20 parts by mass or, preferably, 1 to 15 parts by mass. Among these, particularly preferable are the compounds (1), (2), (8) and (9).

As the component (B), the compounds (1) to (15) may be used singly or two or more of them can be selected and used in combination.

The herbicide composition of the invention may be used together with an insecticide, a fungicide and other herbicides as well as plant growth adjustment agents, fertilizers and the like according to need.

When using the herbicide composition of the invention, the effective ingredients may be used as such but it is preferable to use the composition formulated in the form of a powder agent, hydrated agent, flowable agent, emulsified agent, liquid agent, beads agent, granulated agent or the like by blending a carrier, surfactant, dispersant, auxiliary agent or the like, which are used conventionally in formulations.

As the carrier used for the formulations, for example, solid carriers such as talc, bentonite, clay, kaolin, diatomaceous earth, fumed silica, vermiculite, calcium carbonate, slaked lime, silica sand, ammonium sulfate, urea and the like; and liquid carriers such as isopropyl alcohol, xylene, cyclohexane, methylnaphthalene, water and the like can be exemplified.

As the surfactant and dispersant, for example, alkylbenzenesulfonic acid metal salts, alkylnaphthalenesulfonic acid-formaldehyde condensate product metal salts, alcohol sulfuric acid ester salts, alkylarylsulfonic acid salts, lignin sulfonic acid salts, polyoxyethylene glycol ethers, polyoxyethylene alkylaryl ethers, polyoxyethylene sorbitan monoalkylate and the like can be named. As the auxiliary agent, for example, carboxymethylcellulose, polyethylene glycol, gum Arabic and the like can be named.

When the herbicide composition of the invention is used, it may be dispensed either as such or as diluted to have a concentration depending on the object of use and used for stems-and-leaves treatment by spraying, dispensation to soil or water surface or the like.

The amount of the effective ingredient in a preparation of the herbicide composition of the invention is properly selected according to need. For example, it is selected in a range of 0.01 to 80% by mass or, preferably, 0.05 to 50% by mass, when formulated in the form of a powder agent, beads agent or granular agent. Further, it is selected in a range of 1 to 90% by mass or, preferably, 5 to 80% by mass, when formulated in the form of an emulsified agent, liquid agent, flowable agent or hydrated agent.

The dispensation amount of the herbicide composition of the invention differs depending on the types of the compounds to be used, target weeds, growing tendency of the target weeds, environmental conditions, preparation forms used and the like.

For example, in the case of a powder agent, beads agent or granular agent, the effective ingredient is selected in an amount in the range of 0.1 g to 5 kg or, preferably, 1 g to 1 kg, per 10 ares area.

In the case of using an emulsified agent, liquid agent, flowable agent or hydrated agent after dilution with water, the concentration of the effective ingredient in use is usually selected in the range of 10 to 100,000 ppm.

Hereinafter, the invention will be described in more details by way of Examples but the present invention is never limited thereto in any way.

Example 1

A hydrated agent was prepared by blending 2 parts by mass of 2-[(4,6-dimethoxypyrimidin-2-yl)hydroxymethyl]-6-methoxymethyl-N-difluoromethanesulfonylanilide [hereinafter, referred to as the Compound (A)] with 8 parts by mass of 4-(2-chlorophenyl)-N-cyclohexyl-N-ethyl-4,5-dihydro-5-oxo-1H-tetrazole-1-carboxamide, 0.5 part by mass of polyoxyethylene octylphenyl ether, 0.5 part by mass of β-naphthalene-sulfonic acid-formalin condensate sodium salt, 20 parts by mass of diatomaceous earth and 69 parts by mass of clay and pulverizing the blend thus obtained.

Example 2

A hydrated agent was prepared by blending 1 part by mass of the Compound (A) with 20 parts by mass of methyl 5-(2,4-dichlorophenoxy)-2-nitrobenzoate, 0.5 part by mass of polyoxyethylene octylphenyl ether, 0.5 part by mass of β-naphthalene-sulfonic acid-formalin condensate sodium salt, 20 parts by mass of diatomaceous earth, 5 parts by mass of fumed silica and 53 parts by mass of calcium carbonate and pulverizing the blend thus obtained.

Example 3

A 5 parts by mass portion of lignin sodium sulfonate, 1 part by mass of a polyoxyethylene alkylaryl ether, 3 parts by mass of sodium polycarboxylate, 5 parts by mass of fumed silica, 1 part by mass of α-starch, 65 parts by mass of calcium carbonate and 10 parts by mass of water were added to 10 parts by mass of the Compound (A) and 10 parts by mass of 3-[1-(3,5-dichlorophenyl)-1-methylethyl]-3,4-dihydro-6-methyl-5-phenyl-2H-1,3-oxazin-4-one and the blend was kneaded and granulated by pressing. In the next, the granular product thus obtained was dried by a fluidized bed dryer to prepare a hydrated granular agent.

Example 4

A flowable agent was prepared by adding 2 parts by mass of The Compound (A), 8 parts by mass of S,S'-dimethyl 2-difluoromethyl-4-isobutyl-6-trifluoromethylpyridine-3,5-dicarbothioate, 2 parts by mass of lignin sodium sulfonate, 4 parts by mass of a polyoxyethylene alkylaryl ether ammonium sulfate, 0.5 part by mass of a polyoxyethylene alkylaryl ether, 0.1 part by mass of xanthan gum, 0.5 part by mass of bentonite and 10 parts by mass of ethyleneglycol to 72.9 parts by mass of water, blending the blend by a high-speed agitator and pulverizing the blend by a wet-process pulverizer.

Example 5

A granular agent was prepared by adding 10 parts by mass of water to 1 part by mass of the Compound (A), 14 parts by mass of O-ethyl O-6-nitro-m-tolyl(RS)-sec-butylphosphoramidothioate, 70 parts by mass of an extender (a mixture of talc and bentonite a 1:3 mass proportion), 10 parts by mass of fumed silica and 5 parts by mass of a surface active agent of a mixture of polyoxyethylene sorbitan alkylate, polyoxyethylene alkylaryl polymer and alkylaryl sulfonate, thoroughly blending and kneading the blend thus obtained to give a pasty mixture, then, extruding same through a screen having an opening diameter of 1 mm followed by drying the extruded mixture, and then chopping the product thus obtained in a 0.5 to 1 mm length.

Test Example 1

Weed-Controlling Effect Test by Paddy Field Water-Pooling Treatment

A 1/2000 are wide plastic pot was filled with a paddy field soil and, after shuffling, seeds of each of early watergrass (EC), heartshape false pickerelweed (Mo), rock's bulrush (Si) were sowed, tuberous roots of tidalmarsh flatsedge (Cy) and URIKAWA (Sa) were buried and paddy rice plants (Or) at the two-leaves stage were transplanted followed by pooling of water in a depth of 3 cm. The plants were grown at an average temperature of 22 to 25° C. outdoors and, when the early watergrass grew up to the 2.5 leaves stage, specified amounts of the hydrated agents prepared in the same manner as in Example 1 and diluted with water were dropped into the water pool. Then, plants growing was continued outdoors and the air-dried weights of the respective plant bodies above the soil level were measured on the 15th day after the treatment, and the weed-controlling effects and the degrees of chemical damages were shown as indexes on the basis of the criteria as shown in Table 1. The results are shown in Table 2. The dosages indicated refer to the amounts of the effective ingredients per 10 ares area.

TABLE 1

| Index | Weed-controlling effect and degrees of chemical damages (Growth inhibition degree in portions above soil level) |
|---|---|
| 10 | 95% or higher growth inhibition |
| 9 | not less than 85% but less than 95% growth inhibition |
| 8 | not less than 75% but less than 85% growth inhibition |
| 7 | not less than 65% but less than 75% growth inhibition |
| 6 | not less than 55% but less than 65% growth inhibition |
| 5 | not less than 45% but less than 55% growth inhibition |
| 4 | not less than 35% but less than 45% growth inhibition |
| 3 | not less than 25% but less than 35% growth inhibition |
| 2 | not less than 15% but less than 25% growth inhibition |
| 1 | not less than 5% but less than 15% growth inhibition |
| 0 | not less than 0% but less than 5% growth inhibition |

TABLE 2

| Test compound | Dosage g/10 a. | Weed-controlling effect | | | | | Chemical damages |
| | | Ec | Mo | Si | Cy | Sa | Or |
|---|---|---|---|---|---|---|---|
| A + fentrazamide | 2 + 0 | 8 | 7 | 10 | 8 | 7 | 0 |
| A + fentrazamide | 1 + 0 | 6 | 4 | 8 | 6 | 5 | 0 |
| A + fentrazamide | 0 + 30 | 8 | 3 | 3 | 0 | 1 | 0 |

TABLE 2-continued

| Test compound | Dosage g/10 a. | Weed-controlling effect | | | | | Chemical damages |
|---|---|---|---|---|---|---|---|
| | | Ec | Mo | Si | Cy | Sa | Or |
| A + fentrazamide | 2 + 30 | 10 | 10 | 10 | 10 | 10 | 0 |
| A + fentrazamide | 1 + 30 | 10 | 9 | 10 | 10 | 9 | 0 |
| A + anilofos | 2 + 0 | 8 | 7 | 10 | 8 | 7 | 0 |
| A + anilofos | 0 + 30 | 8 | 2 | 1 | 0 | 0 | 0 |
| A + anilofos | 2 + 30 | 10 | 10 | 10 | 10 | 9 | 0 |
| A + pyributicarb | 2 + 0 | 8 | 7 | 10 | 8 | 7 | 0 |
| A + pyributicarb | 1 + 0 | 6 | 4 | 8 | 6 | 5 | 0 |
| A + pyributicarb | 0 + 60 | 9 | 4 | 0 | 1 | 0 | 0 |
| A + pyributicarb | 2 + 60 | 10 | 10 | 10 | 10 | 9 | 0 |
| A + pyributicarb | 1 + 60 | 10 | 10 | 10 | 10 | 8 | 0 |
| A + bifenox | 2 + 0 | 8 | 7 | 10 | 8 | 7 | 0 |
| A + bifenox | 1 + 0 | 6 | 4 | 8 | 6 | 5 | 0 |
| A + bifenox | 0 + 80 | 0 | 9 | 4 | 1 | 6 | 0 |
| A + bifenox | 2 + 80 | 10 | 10 | 10 | 10 | 10 | 0 |
| A + bifenox | 1 + 80 | 9 | 10 | 10 | 9 | 10 | 0 |
| A + benzobicyclon | 2 + 0 | 8 | 7 | 10 | 8 | 7 | 0 |
| A + benzobicyclon | 1 + 0 | 6 | 4 | 8 | 6 | 5 | 0 |
| A + benzobicyclon | 0 + 20 | 4 | 8 | 10 | 4 | 2 | 0 |
| A + benzobicyclon | 2 + 20 | 10 | 10 | 10 | 10 | 10 | 0 |
| A + benzobicyclon | 1 + 20 | 9 | 10 | 10 | 9 | 9 | 0 |
| A + oxaziclomefone | 2 + 0 | 8 | 7 | 10 | 8 | 7 | 0 |
| A + oxaziclomefone | 0 + 2 | 7 | 0 | 0 | 0 | 0 | 0 |
| A + oxaziclomefone | 2 + 2 | 10 | 9 | 10 | 9 | 9 | 0 |
| A + butamifos | 2 + 0 | 8 | 7 | 10 | 8 | 7 | 0 |
| A + butamifos | 0 + 70 | 8 | 9 | 2 | 1 | 5 | 0 |
| A + butamifos | 2 + 70 | 10 | 10 | 10 | 10 | 10 | 0 |
| A + oxadiargyl | 2 + 0 | 8 | 7 | 10 | 8 | 7 | 0 |
| A + oxadiargyl | 1 + 0 | 6 | 4 | 8 | 6 | 5 | 0 |
| A + oxadiargyl | 0 + 5 | 0 | 9 | 1 | 2 | 5 | 0 |
| A + oxadiargyl | 2 + 5 | 10 | 10 | 10 | 10 | 10 | 0 |
| A + oxadiargyl | 1 + 5 | 9 | 10 | 10 | 10 | 10 | 0 |
| A + dithiopyr | 2 + 0 | 8 | 7 | 10 | 8 | 7 | 0 |
| A + dithiopyr | 0 + 3 | 2 | 6 | 2 | 2 | 0 | 0 |
| A + dithiopyr | 2 + 3 | 10 | 10 | 10 | 10 | 9 | 0 |
| A + pyriminobac-methyl | 1 + 0 | 7 | — | 8 | — | — | 0 |
| A + pyriminobac-methyl | 0 + 1.5 | 6 | — | 0 | — | — | 0 |
| A + pyriminobac-methyl | 1 + 1.5 | 10 | — | 10 | — | — | 0 |

A is 2-[(4,6-dimethoxypyrimidine-2-yl)hydroxy-methyl]-6-methoxymethyl-N-difluoromethane--sulfonylanilide.

INDUSTRIAL APPLICABILITY

By virtue of the synergistic effect between the effective ingredients including 2-[(4,6-dimethoxy-pyrimidine-2-yl)hydroxymethyl]-6-methoxymethyl-N-difluoromethane-sulfonylanilide and at least one kind of the compounds selected from 4-(2-chlorophenyl)-N-cyclohexyl-N-ethyl-4,5-dihydro-5-oxo-1H-tetrazole-1-carboxamide, 3-[1-(3,5-dichlorophenyl)-1-methylethyl]-3,4-dihydro-6-methyl-5-phenyl-2H-1,3-oxazin-4-one, O-3-tert-butylphenyl 6-methoxy-2-pyridyl(methyl)thiocarbamate, O-ethyl O-6-nitro-m-tolyl(RS)-sec-butylphosphoramidothioate, S-4-chloro-N-isopropyl carbaniloyl methyl O,O-dimethyl phosphorodithioate, methyl 5-(2,4-dichlorophenoxy)-2-nitrobenzoate, 5-tert-butyl-3-[2,4-dichloro-5-(prop-2-ynyloxy)phenyl]-1,3,4-oxadiazol-2(3H)-one, 3-(2-chloro-4-mesylbenzoyl)-2-phenylthiobicyclo[3.2.1]oct-2-en-4-one, S,S'-dimethyl 2-difluoromethyl-4-isobutyl-6-trifluoromethylpyridine-3,5-dicarbothioate, S-ethyl azepane-1-carbothioate, 2-amino-3-chloro-1,4-naphthoquinone, methyl 2-[(4,6-dimethoxypyrimidin-2-yl)oxy]-6-[1-(methoxyimino)-ethyl]benzoate, methyl α-(4,6-dimethoxpyrimidin-2-ylcarbamoylsulfamoyl)-o-toluate, ethyl 5-(4,6-dimethoxypyrimidin-2-ylcarbamoylsulfamoyl)-1-methylpyrazole-4-carboxylate and (RS)-7-(4,6-dimethoxy-pyrimidin-2-ylthio)-3-methyl-2-benzofuran-1(3H)-one, the herbicide composition of the present invention gives early appearance of the herbicidal effects which can be accomplished rapidly. A high herbicidal effect is exhibited even with a low dosage along with a broad herbicidal spectrum.

When used as a herbicide for rice crops, the range of appropriate application period is so wide as compared with existing herbicides for rice crops as to exhibit a high herbicidal activity against hardly eliminatable weeds from before germing to the growing stage inhibiting generation of the weeds over a long time still without inhibition of the growth of crop plants. That is, the herbicide composition of the invention is able to inhibit growth of and eliminate annual weeds such as early watergrass, barnyardgrass, smallflower umbrella plant, flaccid flat-sedge, heartshape false pickerelweed, MIZU-AOI, *linderina* species, indian toothcup, threestamen waterwort, jerr-jerry, dopatrium and others, and perennial weeds such as URIKAWA, arrow head (*Sagittaria trifolia*) and the like, pond weed, java water dropwort, tidalmarsh flatsedge, SHIZUI, KUROGUWAI, rock's bulrush, KOUKIYAGARA, needle spikerush and others, growing in paddy fields.

Moreover, the herbicide composition of the present invention has high safety to crops and the safety exhibited to rice crops is particularly high.

The invention claimed is:

1. A herbicide composition containing, as effective ingredients,
   (A) 2-[(4,6-dimethoxypyrimidin-2-yl)hydroxymethyl]-6-methoxymethyl-N-difluoromethanesulfonylanilide; and
   (B) 4-(2-chlorophenyl)-N-cyclohexyl-N-ethyl-4,5-dihydro-5-oxo-1H-tetrazole-1-carboxamide, and
   wherein there is employed, per 1 part by mass of the component (A), 1 to 15 parts by mass of component (B).

2. A method for controlling growth of weeds in a paddy field which comprises sprinkling the herbicide composition described in claim 1 over the paddy field.

3. The method for controlling growth of weeds in a paddy field described in claim 2 in which the herbicide composition is sprinkled in the form of a powder agent or granulated agent in an amount in the range from 0.1 g to 5 kg per 10 ares area of the paddy field.

4. The method for controlling growth of weeds in a paddy field described in claim 2 in which the herbicide composition is sprinkled in the form of an emulsified agent, liquid agent, flowable agent or hydrated agent, the concentration of the components (A) and (B) as a total therein being in the range from 10 to 100,000 ppm.

* * * * *